United States Patent
Ostgard et al.

(10) Patent No.: US 6,747,180 B2
(45) Date of Patent: Jun. 8, 2004

(54) METAL CATALYSTS

(75) Inventors: Daniel Ostgard, Kleinostheim (DE); Peter Panster, Rodenbach (DE); Claus Rehren, Aschaffenburg (DE); Monika Berweiler, Maintal (DE); Günter Stephani, Grosserkmannsdorf (DE); Lothar Schneider, Coswig (DE)

(73) Assignees: Degussa AG, Düsseldorf (DE); Fraunhofer-Gesellschaft zur Föderung der Angewandten Forschung E.V., München (DE)

( * ) Notice: Subject to any disclaimer, the term of this patent is extended or adjusted under 35 U.S.C. 154(b) by 0 days.

(21) Appl. No.: 10/417,864

(22) Filed: Apr. 17, 2003

(65) Prior Publication Data

US 2003/0211938 A1 Nov. 13, 2003

Related U.S. Application Data

(62) Division of application No. 09/618,101, filed on Jul. 17, 2000, now Pat. No. 6,573,213.
(60) Provisional application No. 60/145,703, filed on Jul. 27, 1999.

(30) Foreign Application Priority Data

Jul. 16, 1999 (DE) .......................................... 199 33 450

(51) Int. Cl.$^7$ ................................................. C07C 5/00
(52) U.S. Cl. ........................... 585/250; 585/252; 502/8; 502/325; 502/326; 502/327; 502/328; 502/329; 502/301; 502/527.24
(58) Field of Search ................................. 585/252, 250; 502/8, 325, 326, 327, 328, 329, 527.24, 301

(56) References Cited

U.S. PATENT DOCUMENTS

| | | | | |
|---|---|---|---|---|
| 3,907,710 A | * | 9/1975 | Lundsager | .................. 502/262 |
| 4,039,480 A | | 8/1977 | Watson | |
| 4,089,812 A | | 5/1978 | O'Hare et al. | |
| 4,576,926 A | | 3/1986 | Wang et al. | |
| 4,804,796 A | | 2/1989 | Wang et al. | |
| 4,826,799 A | | 5/1989 | Cheng et al. | |
| 4,917,857 A | | 4/1990 | Jaeckel et al. | |
| 6,573,213 B1 | * | 6/2003 | Ostgard et al. | .............. 502/301 |

FOREIGN PATENT DOCUMENTS

| | | |
|---|---|---|
| DE | 23 53 631 | 5/1975 |
| DE | 35 35 483 | 4/1987 |
| EP | 0 300 543 | 1/1989 |
| FR | 2 172 755 | 10/1973 |

OTHER PUBLICATIONS

European Search Report, issued by the European Patent Office, dated Sep. 6, 2000, for European Patent Application No. EP 00115180.2. (3 pages).

* cited by examiner

*Primary Examiner*—William Cheung
(74) *Attorney, Agent, or Firm*—Smith, Gambrell & Russell, LLP

(57) ABSTRACT

Metal catalysts comprising hollow forms or spheres are made of metal alloy and optionally activated. The metal catalysts can be used for the hydrogenation, dehydrogenation, isomerization reductive alkylation, reductive amination, and/or hydration reaction of organic compounds.

11 Claims, No Drawings

METAL CATALYSTS

REFERENCE TO RELATED APPLICATION

This application is a divisional patent application of our copending patent application Ser. No. 09/618,101, filed Jul. 17, 2000, now U.S. Pat. No. 6,573,213 B1 which in turn claims the benefit of provisional application 60/145,703 of Jul. 27, 1999, now expired, which are both relied on and incorporated herein by reference.

INTRODUCTION AND BACKGROUND

The present invention relates to metal catalysts.

Activated metal catalysts are known in the field of chemical engineering as Raney catalysts. They are used, largely in powder form, for a large number of hydrogenation, dehydrogenation, isomerization and hydration reactions of organic compounds. These powdered catalysts are prepared from an alloy of a catalytically-active metal, also referred to herein as a catalyst metal, with a further alloying component which is soluble in alkalis. Mainly nickel, cobalt, copper, or iron are used as catalyst metals. Aluminum is generally used as the alloying component which is soluble in alkalis, but other components may also be used, in particular zinc and silicon or mixtures of these with aluminum.

These so-called Raney alloys are generally prepared by the ingot casting process. In that process a mixture of the catalyst metal and, for example, aluminum are first melted and casted into ingots. Typical alloy batches on a production scale amount to about ten to one hundred kg per ingot. According to DE 21 59 736 cooling times of up to two hours were obtained. This corresponds to an average rate of cooling of about 0.2/s. In contrast to this, rates of 102 to 106 K/s are achieved in processes where rapid cooling is applied (for example, an atomizing process). The rate of cooling is affected in particular by the particle size and the cooling medium (see Materials Science and Technology edited by R. W. Chan, P. Haasen, E. J. Kramer, Vol. 15, Processing of Metals and Alloys, 1991, VCH-Verlag Weinheim, pages 57 to 110). A process of this type is used in EP 0 437 788 B 1 in order to prepare a Raney alloy powder. In that process the molten alloy at a temperature of 50 to 500° C. above its melting point is atomized and cooled using water and/or a gas.

To prepare a catalyst, the Raney alloy is first finely milled if it has not been produced in the desired powder form during preparation. Then the aluminum is entirely or partly removed by extraction with alkalis such as, for example, caustic soda solution. This activates the alloy powder. Following extraction of the aluminum the alloy power has a high specific surface area (BET), between 20 and 100 $m^2/g$, and is rich in active hydrogen. The activated catalyst powder is pyrophoric and stored under water or organic solvents or is embedded in organic compounds which are solid at room temperature.

Powdered catalysts have the disadvantage that they can be used only in a batch process and, after the catalytic reaction, have to be separated from the reaction medium by costly sedimentation and/or filtration. Therefore a variety of processes for preparing molded items which lead to activated metal fixed-bed catalysts after extraction of the aluminum have been disclosed. Thus, for example, coarse particulate Raney alloys, i.e., Raney alloys which have only been coarsely milled, are obtainable and these can be activated by a treatment with caustic soda solution. Extraction and activation then occurs only in a surface layer the thickness of which can be adjusted by the conditions used during extraction.

A substantial disadvantage of catalysts prepared by these prior methods are the poor mechanical stability of the activated outer layer. Since only this outer layer of the catalysts is catalytically active, abrasion leads to rapid deactivation and renewed activation of deeper lying layers of alloy using caustic soda solution then leads at best to partial reactivation.

Patent application EP 0 648 534 B1 describes shaped, activated Raney metal fixed-bed catalysts and their preparation. These catalysts avoid the disadvantages described above, e.g., the poor mechanical stability resulting from activating an outer layer. To prepare these catalysts, a mixture of powers of a catalyst alloy and a binder are used. In the catalyst alloys each contain at least one catalytically active catalyst metal and an extractable alloying component. The pure catalyst metals or mixtures thereof which do not contain extractable components are used as binder. The use of the binder in an amount of 0.5 to 20 weight percent with respect to the catalyst alloy, is essential in order to achieve sufficient mechanical stability after activation.

After shaping the catalyst alloy and the binder with conventional shaping aids and pore producers, the freshly prepared items which are obtained are calcined at temperatures below 850° C. As a result of sintering processes in the finely divided binder, this produces solid compounds between the individual granules of the catalysts alloy. These compounds, in contrast to catalyst alloys, are non-extractable or only extractable to a small extent so that a mechanically stable structure is obtained even after activation.

However, the added binder has the disadvantage that it is substantially catalytically inactive and thus the number of active centers in the activated layer is reduced. In addition, the absolutely essential use of a binder means that only restricted range of amounts of pore producers can be used without endangering the strength of the shaped item. For this reason, the bulk density of these catalysts cannot be reduced to a value of less than 1.9 kg per liter without incurring loss of strength. This leads to a considerable economic disadvantage when using these catalysts in industrial processes.

In particular when using more expensive catalysts alloys, for example cobalt alloys, the high bulk density leads to a high investment per reactor bed, which is, however partly compensated for by the high activity and long-term stability of these catalyst. In certain cases, the high bulk density of the catalyst also requires a mechanically reinforced reactor structure.

An object of the present invention is therefore to provide activated base metal catalysts from hollow metallic forms which largely avoids the disadvantages of the above known fixed-bed catalysts.

SUMMARY OF THE INVENTION

The above and other objects of the invention can be achieved by producing hollow forms out of the desired alloys and activating then in order to make the catalyst. The major advantages of this invention are the low bulk density and high activity per gram of metal exhibited by these catalysts.

It is a feature of the present invention that the metal catalyst are hollow forms. Preferably the hollow forms are hollow spheres. These spheres can exhibit a diameter of 0.5 to 20 mm and a wall thickness of 0.1 to 5 mm.

The shell of the spheres can be impermeable or it can show an open porosity up to 80%.

The shell of the spheres can consist of different layers and/or the metal can be graduated.

The metal catalysts comprising hollow forms can be activated.

Another feature of the present invention is a process for the for the production of the metal catalysts comprising spraying of metal powders, optionally together with a binder on to forms consisting of a burnable or combustible material; i.e. polystyrene foam (styrofoam), and burning out the material to obtain the hollow form.

In another feature of the present invention, the process for the production of the metal catalysts is carried out by using metal powders consisting of a rapidly cooled alloy. The rapidly cooled alloy can be made according to commonly used methods such spray drying in various atmospheres as well as rapidly cooling in liquids such as water. The hollow form consisting of the alloy and optionally a binder can then be activated with an alkali solutions such as aqueous NaOH, to form the activated catalyst.

One of the metal powders can consist of a slowly cooled alloy. The hollow form consisting of the alloy and optionally a binder can then be activated with an alkali solution, such as an aqueous NaOH solution, to form the activated catalyst; i.e. the activated state. Prior to activation, the catalyst can be referred to as being in the unactivated form.

In the process for the production of the metal catalysts the alloy can consist of one or more catalytic metal such as nickel, iron, copper, palladium, ruthenium, and cobalt; an alkali soluble alloying component such as aluminum, zinc, and silica; and optionally one or more promoter elements such as Cr, Fe, Ti, V, Ta, Mo, Mg, Co, and/or W.

DETAILED DESCRIPTION OF THE INVENTION

The hollow spheres according to this invention can be prepared according to the method disclosed by Andersen, Schneider, and Stephani (See, "Neue Hochporöse Metallische Werkstoffe", Ingenieur-Werkstoffe, 4, 1998, pages 36–38 incorporated herein by reference). In this method, a mixture of the desired alloy, an organic binder, and optionally an inorganic binder were sprayed uniformly through a fluidized bed of polystyrene foam (styrofoam) balls where it coats the polystyrene foam. The coated balls are then calcined at optionally temperatures ranging from 450 to 1000° C. to burn out the polystyrene foam followed by a higher calcination temperature to sinter the metal together in order to make the hollow form more stable. After calcination, the catalyst is then activated by a caustic soda solution to produce the activated base metal catalyst. An added benefit to this catalyst system is that one can easily control the thickness of the hollow form's walls from the coating conditions and the porosity of this wall by the particle size and composition of the original powder mixture.

The bulk density of the resulting fixed bed catalyst is very important for highly active catalysts. While the known standard fixed bed activated base metal catalysts have bulk densities ranging from 2.4 to 1.8 kg/l, bulk densities similar to other fixed bed applications such as 0.3 to 1.0 kg/l are highly desirable to keep the cost to fill a commercial reactor at a minimum.

The ratio by weight of catalyst metal to extractable alloying component in the catalyst alloy is, as is conventional with Raney alloys, in the range from 20:80 to 80:20. Catalysts according to the invention may also be doped with other metals in order to have an effect on the catalytic properties. The purpose of this type of doping, is for example, to improve the selectivity in a specific reaction. Doping metals are frequently also called promoters. The doping or promoting of Raney catalyst is described for example in U.S. Pat. No. 4,153, 578 and DE-AS 21 01 856 in DE-OS 21 00 373 and in the DE-AS 2053799.

In principle, any known metal alloys such as nickel-aluminum, cobalt-aluminum, copper-aluminum, nickel-chrom-iron-aluminum can be used. This means any Raney-type alloys that involved the combination of leachable materials such as zinc, silicon and/or aluminum in combination with catalytic materials such as nickel, cobalt, copper, and/or iron can be used.

The alloys can contain doping materials like chromium, iron, titanium, vanadium, tantalum with extractable elements such as aluminum, zinc and silicon may be used for the present invention. Suitable promoters are transition elements in groups of 3B to 7B and 8 and group 1B of the Periodic Table of Elements and also the rare-earth metals. They are also used in an amount of up to 20 wt %, with respect of the total weight of catalyst. Chromium, manganese, iron, cobalt, vanadium, tantalum, titanium, tungsten, and/or molybdenum and metals from platinum group are preferably used as promoters. They are expediently added as alloying constituents in the catalyst alloy. In addition, promoters with a different extractable metal alloy, in the form of a separable metal powder, may be used, or the promoters may be applied later to the catalyst's material. Later application of promoters may be performed either after calcination or after activation. Optimum adjustment of the catalyst properties to the particular catalyst process is thus possible.

The Raney type catalyst precursors resulting from calcination are also very important with regard the economic viability of invention. They are not pyrophoric and can be handled and transported without difficulty. Activation can be performed by the user shortly before use. Storage under water or organic solvents or embedding in organic compounds is not required for the catalyst precursors.

The metal catalysts of the invention can be used for the hydrogenation, dehydrogenation, isomerization and/or hydration reaction of organic compounds.

Comparison Example 1

A free-flowing, pelletalizable catalyst mixture was prepared in accordance with the instructions in EP 0 648 534 A1 for a comparison catalyst consisting of 1000 g of 53% Ni and 47% Al alloy powder, 150 g of pure nickel powder (99% Ni, and d50=21*m), and 25 g of ethylene bis-stearoylamide whilst adding about 150 g of water. Tablets with the diameter of 4 mm and a thickness of 4 mm were compressed from this mixture. The shaped items were calcined for 2 h at 700° C. The tablets were activated in 20% strength caustic soda solution for 2 hours at 80° C. after calcination. Under the conditions of application example, this catalyst started to hydrogenate nitrobenzene at 120° C. and the activity was 1.36 ml of consumed hydrogen per gram of catalyst per minute.

EXAMPLE 1

A coating solution was prepared by suspending 600 grams of a rapidly cooled 50% Ni/50% Al alloy in a 800 ml aqueous solution containing 5 wt % polyvinylalcohol and 1.25 wt % glycerin. This suspension was then sprayed onto 1500 ml of polystyrene balls ranging from 4 to 5 mm while they were suspended in an upwardly flowing air steam. After coating the polystyrene foam balls with the above mentioned solution, the balls were then dried in upwardly flowing air at temperatures up to 80° C. (higher temperatures can also be used). These dried coated polystyrene foam spheres had a bulk density of 0.45 g/ml and half of these spheres were further coated with an alloy solution so as to demonstrate the flexibility of this process.

The solution for the second layer consisted of 700 grams of a rapidly cooled 50% Ni/50% Al alloy that was suspended in a 800 ml aqueous solution containing 5 wt % polyvinylalcohol and 1.25 wt % glycerin. This suspension was then sprayed onto 750 ml of the Ni/Al precoated and dried polystyrene foam balls mentioned above while they were suspended in an upwardly flowing air stream. After coating the polystyrene foam balls with the above mentioned solution, the balls were then dried in upwardly flowing air at temperatures up to 80° C. (higher temperatures can also be used).

Although the solution for the second layer was similar to the first, this technique clearly demonstrates the ability of this process to make layered hollow spheres. The dried coated spheres were then heated in a controlled nitrogen/air stream at 830° C. for 1 hour to burn out the polystyrene foam and to sinter together the alloy particles. The hollow spheres were then activated in a 20 wt % NaOH solution for 1.5 hours at 80° C. The resulting activated hollow spheres had diameters ranging from 5 to 6 mm, a shell thickness range of 700–1000*, a crush strength of 90 N, and the bulk density of 0.62 g/ml.

Under the conditions of utilization example 1 herein below, this catalyst started to hydrogenate nitrobenzene at 110–120° C. and the catalyst's nitrobenzene activity was 1.54 ml of consumed hydrogen per gram of catalyst per minute.

EXAMPLE 2

A coating solution was prepared by suspending 500 grams of a rapidly cooled 50% Ni/50% Al alloy and 37.5 grams of nickel powder in a 750 ml aqueous solution containing 5 wt % polyvinylalcohol and 1.25 wt % glycerin. This suspension was then sprayed onto 1000 ml of polystyrene foam balls ranging from 4 to 5 mm while they were suspended in an upwardly flowing air stream. After coating the polystyrene foam balls with the above mentioned solution, the balls were then dried in upwardly flowing air at temperatures up to 80° C. (higher temperatures can also be used). The dried coated spheres were then heated in a controlled nitrogen/air stream at 840° C. for 1 hour to burn out the polystyrene foam and to sinter together the nickel and alloy particles.

The hollow spheres were then activated in a 20 wt % NaOH solution for 1.5 hours at 80° C. The resulting activated hollow spheres had diameters ranging from 5 to 6 mm, an average shell thickness of 500*, and the bulk density of 0.34 g/ml.

Under the conditions of utilization example 1, this catalyst started to hydrogenate nitrobenzene at 110–120° C. and the catalyst's nitrobenzene activity was 1.82 ml of consumed hydrogen per gram of catalyst per minute.

EXAMPLE 3

A coating solution was prepared by suspending 800 grams of a 50% Co/50% Al alloy in a 1000 ml aqueous solution containing 5 wt % polyvinylalcohol and 1.25 wt % glycerin. This suspension was then sprayed onto 2000 ml of polystyrene foam balls ranging from 4 to 5 mm while they were suspended in an upwardly air stream. After coating the polystyrene foam balls with the above mentioned solution, the balls were then dried in upwardly flowing air at temperatures up to 80° C. (higher temperatures can also be used). These dried coated styrofoam spheres had a bulk density of 0.35 g/ml and half of these spheres were further coated with an alloy solution.

The solution for the second layer consisted of 800 grams of a 50% Co/50% Al alloy that was suspended in a 1000 ml aqueous solution containing 5 wt % polyvinylalcohol and 1.25 wt % glycerin. This suspension was then sprayed onto 1000 ml of the Co/Al precoated and dried polystyrene foam balls mentioned above while they were suspended in an upwardly air stream. After coating the polystyrene foam balls with the above mentioned solution, the balls were then dried in upwardly flowing air at temperatures up to 80° C. (higher temperatures can also be used). The dried coated spheres were then heated in a controlled nitrogen/air stream at 700° C. to burn out the polystyrene foam and to sinter together the alloy particles.

The hollow spheres were then activated in a 20 wt % NaOH solution for 1.5 hours at 80° C. The resulting activated hollow spheres had diameters ranging from 5 to 6 mm, a shell thickness of 700*, a crush strength of 71 N, and the bulk density of 0.50 g/ml. As could be visually seen from the evolution of hydrogen bubbles, the catalyst had a large reservoir of active hydrogen.

EXAMPLE 4

A coating solution was prepared by suspending 800 grams of a 50% Cu/50% Al alloy and 104 grams of copper powder in a 1000 ml aqueous solution containing 5 wt % polyvinylalcohol and 1.25 wt % glycerin. This suspension was then sprayed onto 2000 ml of polystyrene foam balls ranging from 4 to 5 mm while they were suspended in an upwardly flowing air stream. After coating the polystyrene foam balls with the above mentioned solution, the balls were then dried in upwardly flowing air at temperatures up to 80° C. (higher temperatures can also be used). These dried coated polystyrene foam spheres had a bulk density of 0.26 g/ml and half of these spheres were further coated with an alloy solution.

The solution for the second layer consisted of 800 grams of a 50% Cu/50% Al alloy and 104 grams of copper powder that were suspended in a 1000 ml aqueous solution containing 5 wt % polyvinylalcohol and 1.25 wt % glycerin. This suspension was then sprayed onto 1000 ml of the Cu/Al precoated and dried polystyrene foam balls mentioned above while they were suspended in an upwardly flowing air stream. After coating the polystyrene foam balls with the above mentioned solution, the balls were then dried in upwardly flowing air at temperatures up to 80° C. (higher temperatures can also be used). The dried coated spheres were then heated in a controlled nitrogen/air stream at 550° C. to burn out the polystyrene foam and to sinter together the copper and alloy particles.

The hollow spheres were then activated in a 20 wt % NaOH solution for 1.5 hours at 80° C. The resulting activated hollow spheres had an average diameter 6 mm, a shell thickness ranging from 600 to 700*, and the bulk density of 0.60 g/ml. As could be visually seen from the evolution of hydrogen bubbles, the catalyst had a large reservoir of active hydrogen.

EXAMPLE 5

A coating solution was prepared by suspending 800 grams of a slowly cooled 50% Ni/0.5% Fe/1.2% Cr/48.3% Al alloy and 60 grams of nickel powder in a 1000 ml aqueous solution containing 5 wt % polyvinylalcohol and 1.25 wt % glycerin. This suspension was then sprayed onto 2000 ml of polystyrene foam balls ranging from 4 to 5 mm while they were suspended in an upwardly flowing air stream. After coating the polystyrene foam balls with the above mentioned solution, the balls were then dried in upwardly flowing air at temperatures up to 80° C. (higher temperatures can also be used). These dried coated polystyrene foam spheres had a bulk density of 0.30 g/ml and half of these spheres were further coated with an alloy solution.

The solution for the second layer consisted of 800 grams of a slowly cooled 50% Ni/0.5% Fe/1.2% Cr/48.3% Al alloy and 60 grams of nickel powder that were suspended in a 1000 ml aqueous solution containing 5 wt % polyvinylalcohol and 1.25 wt % glycerin. This suspension was then sprayed onto 1000 ml of the Ni/Fe/Cr/Al precoated and dried polystyrene foam balls mentioned above while they were suspended in an upwardly flowing air stream. After coating the polystyrene foam balls with the above mentioned solution, the balls were then dried in upwardly flowing air at temperatures up to 80° C. (higher temperatures can also be used). The dried coated spheres were then heated in a controlled nitrogen/air stream at 700° C. to burn out the polystyrene foam and to sinter together the nickel and alloy particles.

The hollow spheres were then activated in a 20 wt % NaOH solution for 1.5 hours at 80° C. The resulting activated hollow spheres had an average diameter 5.9 mm, a shell thickness of 700*, the crush strength of 85 N, and the bulk density of 0.55 g/ml.

Under the conditions of utilization example 1, this catalyst started to hydrogenate nitrobenzene at 110° C. and the catalyst's nitrobenzene activity was 2.40 ml of consumed hydrogen per gram of catalyst per minute.

EXAMPLE 6

A coating solution was prepared by suspending 1000 grams of a rapidly cooled 50% Ni/50% Al alloy and 75 grams of nickel powder in a 1000 ml aqueous solution containing 5 wt % polyvinylalcohol and 1.25 wt % glycerin. This suspension was then sprayed onto 2000 ml of polystyrene foam balls ranging from 2 to 3 mm while they were suspended in an upwardly flowing air stream. After coating the polystyrene foam balls with the above mentioned solution, the balls were then dried in upwardly flowing air at temperatures up to 80° C. (higher temperatures can also be used). These dried coated polystyrene foam spheres had a bulk density of 0.33 g/ml and half of these spheres were further coated with an alloy solution.

The solution for the second layer consisted of 1000 grams of a rapidly cooled 50% Ni/50% Al alloy and 75 grams of nickel powder that were suspended in a 1000 ml aqueous solution containing 5 wt % polyvinylalcohol and 1.25 wt % glycerin. This suspension was then sprayed onto 1000 ml of the Ni/Al precoated and dried polystyrene foam balls mentioned above while they were suspended in an upwardly flowing air stream. After coating the polystyrene foam balls with the above mentioned solution, the balls were then dried in upwardly flowing air at temperatures up to 80° C. (higher temperatures can also be used). These dried double-coated polystyrene foam spheres had a bulk density of 0.75 g/ml and half of these spheres were once again coated further with a third addition of the alloy solution. The solution for the third layer consisted of 1000 grams of a rapidly cooled 50% Ni/50% Al alloy and 75 grams of nickel powder that were suspended in a 1000 ml aqueous solution containing 5 wt % polyvinylalcohol and 1.25 wt % glycerin. This suspension was then sprayed onto 500 ml of the Ni/Al double-precoated and dried polystyrene foam balls mentioned above while they were suspended in an upward air steam. After coating the polystyrene foam balls with the above mentioned solution, the balls were then dried in upwardly flowing air at temperatures up to 80° C. (higher temperatures can also be used). The dried triple-coated spheres were then heated in a controlled nitrogen/air stream at 700° C. to burn out the polystyrene foam and to sinter together the nickel and alloy particles.

The hollow spheres were then activated in a 20 wt % NaOH solution for 1.5 hours at 80° C. The resulting activated hollow spheres had an average diameter 4.5 mm, a shell thickness of 600 to 700*, and the bulk density of 0.85 g/ml.

Under the conditions of utilization example 1, this catalyst started to hydrogenate nitrobenzene at 78° C. and the catalyst's nitrobenzene activity was 3.46 ml of consumed hydrogen per gram of catalyst per minute.

Utilization Example 1

The catalytic activity of the catalyst from comparison examples 1 and 2 and from examples 1 to 5 were compared during the hydrogenation of nitrobenzene. For this purpose, 100 g of nitrobenzene and 100 g of ethanol were placed in a stirred autoclave with a capacity of 0.51, fitted with a gas stirrer. 10 g of the catalyst being investigated were suspended each time in the stirred autoclave using a catalyst basket so that the catalyst material was thoroughly washed by the reactant/solvent mixture, and hydrogen was introduced. Hydrogenation was performed at a hydrogen pressure of 40 bar and a temperature of 150° C. The initiation temperature and the rate of hydrogen consumption were determined. The results are given in table 1. As a check, samples were withdrawn after 1, 2, 3, 4, and 5 h and analyzed using gas chromatography.

Further variations and modifications of the foregoing will be apparent to those skilled in the art and are intended to be encompassed by the claims appended hereto.

German priority application 199 33 450.1 is relied on and incorporated herein by reference.

TABLE 1

The Hydrogenation of Nitrobenzene to Aniline.

| Catalyst | Active metal | Promoters | Inorgane binders | Bulk Density, kg/l | Initiation Temperature, ° C. | Rate of Hydrogen Consumption, ml $H_2$/(h)(g of cat.) |
|---|---|---|---|---|---|---|
| CE1 | Ni | — | Ni powder | 2.3 | 125 | 1.36 |
| E1 | Ni | — | — | 0.62 | 110–120 | 1.54 |
| E2 | Ni | — | Ni powder | 0.34 | 110–120 | 1.82 |

TABLE 1-continued

The Hydrogenation of Nitrobenzene to Aniline.

| Catalyst | Active metal | Promoters | Inorgane binders | Bulk Density, kg/l | Initiation Temperature, °C | Rate of Hydrogen Consumption, ml $H_2$/(h)(g of cat.) |
|---|---|---|---|---|---|---|
| E5 | Ni | Cr, Fe | Ni powder | 0.55 | 110 | 2.40 |
| E6 | Ni | — | Ni powder | 0.85 | 78 | 3.46 |

What is claimed is:

1. A process for the hydrogenation, dehydrogenation, isomerization and/or hydration reaction of organic compounds comprising reacting said organic compounds in the presence of an activated Raney metal catalyst comprising hollow spheres, wherein said spheres have a shell which is impermeable.

2. The process according to claim 1, wherein said spheres have a shell which has an open porosity of a maximum of about 80%.

3. The process according to claim 1, wherein said spheres have a shell which consists of different layers.

4. The process according to claim 1, wherein said spheres have a shell which is layered.

5. The process according to claim 1, wherein the activated Raney metal catalyst comprises a catalyst metal selected from the group consisting of nickel, cobalt, copper, iron, palladium, ruthenium and mixtures thereof; and an alloying component.

6. The process according to claim 5, wherein said alloying component is a member selected from the group consisting of aluminum, zinc, silicon and mixtures thereof.

7. The process according to claim 6, which additionally comprises a promoter.

8. A process for the hydrogenation of nitrobenzene comprising forming a reaction solution by mixing nitrobenzene and an inert organic solvent, suspending an activated Raney metal catalyst in said reaction solution, introducing hydrogen into said reaction solution and thereby carrying out a hydrogenation reaction.

9. A process for the dehydrogenation of an organic compound comprising reacting said organic compound with a dehydrogenation agent in the presence of an activated Raney metal catalyst in the form of hollow spheres.

10. A process for the isomerization of an organic compound comprising reacting said organic compound with an isomerization agent in the presence of an activated Raney metal catalyst in the form of hollow spheres.

11. A process for the hydration of an organic compound comprising reacting said organic compound with a hydration agent in the presence of an activated Raney metal catalyst in the form of hollow spheres.

* * * * *